United States Patent
Buttle

(10) Patent No.: US 9,851,265 B2
(45) Date of Patent: Dec. 26, 2017

(54) APPARATUS AND METHOD FOR MEASURING PROPERTIES OF A FERROMAGNETIC MATERIAL

(71) Applicant: MAPS Technology Limited, Abingdon, Oxfordshire (GB)

(72) Inventor: David John Buttle, Abingdon (GB)

(73) Assignee: GE Oil & Gas UK Limited, Nailsea (GB)

( * ) Notice: Subject to any disclaimer, the term of this patent is extended or adjusted under 35 U.S.C. 154(b) by 108 days.

(21) Appl. No.: 14/377,298

(22) PCT Filed: Jan. 24, 2013

(86) PCT No.: PCT/GB2013/050148
§ 371 (c)(1),
(2) Date: Aug. 7, 2014

(87) PCT Pub. No.: WO2013/117904
PCT Pub. Date: Aug. 15, 2013

(65) Prior Publication Data
US 2015/0008908 A1     Jan. 8, 2015

(30) Foreign Application Priority Data
Feb. 8, 2012 (GB) .................................. 1202184.6

(51) Int. Cl.
*H01F 38/14* (2006.01)
*G01N 27/72* (2006.01)
(Continued)

(52) U.S. Cl.
CPC ............ *G01L 1/127* (2013.01); *G01L 5/0047* (2013.01); *G01N 27/72* (2013.01); *G01N 27/9033* (2013.01); *G01R 33/12* (2013.01)

(58) Field of Classification Search
CPC .... F16K 31/082; G03F 7/70758; H01F 7/081; H01F 7/122; H01F 38/14; H01F 41/0253;
(Continued)

(56) References Cited

U.S. PATENT DOCUMENTS

| 5,992,241 A | * | 11/1999 | Posgay | ................ | G01N 27/725 |
| | | | | | 324/209 |
| 8,283,918 B2 | * | 10/2012 | Park | ..................... | B24B 49/105 |
| | | | | | 324/220 |
| 2002/0186023 A1 | * | 12/2002 | Kliman | .................. | G01R 31/34 |
| | | | | | 324/546 |

FOREIGN PATENT DOCUMENTS

| CN | 101246143 | * | 8/2008 | |
| CN | 101246143 A | | 8/2008 | |

(Continued)

OTHER PUBLICATIONS

International Search Report issued in connection with corresponding WO Application PCT/GB2013/050148 on Jun. 24, 2013.
(Continued)

*Primary Examiner* — Alesa Allgood
(74) *Attorney, Agent, or Firm* — GE Global Patent Operation

(57) ABSTRACT

An apparatus for measuring material properties of an object of ferromagnetic material, the apparatus including a probe, the probe including an electromagnet core defining two spaced-apart poles for inducing a magnetic field in the object, and a drive coil wound around the electromagnet core, and means to supply an alternating electric current to the drive coil to generate an alternating magnetic field in the electromagnet core and consequently in the object, wherein the probe also includes two sensing coils arranged in the vicinity of each of the poles, for sensing the magnetic flux density that links the core and the object, such sensing coils (Continued)

are significantly more sensitive to changes in material properties than are sensing coils overwound onto the drive coil.

22 Claims, 3 Drawing Sheets

(51) Int. Cl.
    *G01L 1/12* (2006.01)
    *G01N 27/90* (2006.01)
    *G01L 5/00* (2006.01)
    *G01R 33/12* (2006.01)

(58) Field of Classification Search
CPC .. H01F 7/066; H01F 3/00; H01F 5/003; H02J 7/025; H02J 7/0027; B60R 21/0136; B60R 21/0134; B24B 37/013; A61B 1/00158; A61B 17/1707; Y02B 60/50; G01L 3/102; G01L 1/127; G01R 33/04; G01R 33/12; G01R 33/09; G01R 31/08; G01R 33/0094; G01N 27/82; G01N 27/90; G01N 27/902; G01N 27/9033; G01N 27/904; G01N 29/265; E21B 47/0006; E21B 47/00; E21B 47/06

USPC ........ 324/220, 209, 232, 238, 240, 242, 262
See application file for complete search history.

(56) References Cited

FOREIGN PATENT DOCUMENTS

| | | | |
|---|---|---|---|
| EP | 1436604 | A2 | 7/2004 |
| GB | 1432160 | * | 4/1976 |
| GB | 1432160 | A | 4/1976 |
| GB | 2278450 | A | 11/1994 |
| JP | 57100330 | * | 6/1982 |
| JP | 57100330 | A | 6/1982 |
| JP | 2004037217 | A | 2/2004 |
| WO | 8705112 | A1 | 8/1987 |
| WO | 0210737 | A2 | 2/2002 |
| WO | 03034054 | A2 | 4/2003 |

OTHER PUBLICATIONS

Great Britain Search Report issued in connection with corresponding GB Application No. 1202184.6 dated May 9, 2012.

* cited by examiner

APPARATUS AND METHOD FOR MEASURING PROPERTIES OF A FERROMAGNETIC MATERIAL

BACKGROUND OF THE INVENTION

Field of the Invention

Embodiments of the present invention relate to an apparatus and a method for measurement of properties of a ferromagnetic material, for example for measuring stress.

Description of the Related Art

The stresses in structures such as rails, bridges and pipelines, complex mechanisms such as vehicles and machinery, or simple devices such as struts, cables or bearings arise from various causes including changes of temperature, and the loads and pressures due to use. There may also be residual stresses arising from the fabrication of the structure or device. In some situations (such as pipelines) the principal stress directions can be expected to be in particular directions (circumferential and longitudinal), whereas in other situations the principal stress directions are also unknown. A variety of magnetic techniques are known to have some sensitivity to stress, although magnetic measurements are usually also affected by other material properties such as microstructure. A way of measuring stress in a steel plate is described in GB 2 278 450, this method using a probe containing a U-shaped electromagnetic core with two spaced-apart poles and with a drive coil wound around the middle of the core to generate an alternating magnetic field in the plate, and then combining measurements from two sensors, one being a measure of stress-induced magnetic anisotropy, and the other being a measure of directional effective permeability (DEP). The latter is sensed by a sensing coil that is also wound around the middle of the core. Such electromagnetic measurements are affected not only by material properties, but also by geometrical factors, in particular the lift off from the surface (i.e. the gap between the probe and the surface). Ways of eliminating the effect of lift off are described in EP 1 436 604=WO 03/034054, describing both a graphical and an algebraic procedure.

A more sensitive way of sensing material properties, such as stress, would be desirable.

BRIEF SUMMARY OF THE INVENTION

According to the present invention there is provided an apparatus for measuring material properties of an object of ferromagnetic material, the apparatus comprising: a probe, the probe comprising an electromagnet core defining two spaced-apart poles for inducing a magnetic field in the object, and a drive coil wound around the electromagnet core; means to supply an alternating electric current to the drive coil to generate an alternating magnetic field in the electromagnet core and consequently in the object; and two sensing coils, one arranged in the vicinity of each of the poles, for sensing the magnetic flux density that links the core and the object.

The sensing coils may be on the faces of the poles, so that in use each coil is between the face of the pole and the surface of the object. In this case there may be a plurality of sensing coils on the face of each pole; in some applications this provides greater resolution. Alternatively the sensing coils may be wound around the core adjacent to the poles. Surprisingly such sensing coils are considerably more sensitive to changes in stress in the object than are sensing coils at the middle of the electromagnet core.

In an arrangement according to an embodiment, the sensing coils in the vicinity of the poles are matched, and are connected in series to provide an output. If the coils are wound or connected such that equal magnetic field changes directed towards the two poles would produce no net output, then this arrangement ensures that any external magnetic field changes are not sensed; the probe will only be sensitive to the magnetic field generated by the drive coil, as this produces magnetic field directions that are opposite at the two poles.

In a modification, the probe may comprise a plurality of sensing coils in the vicinity of each of the poles, for sensing the magnetic flux density that links the core and the object, the sensing coils being at different distances from the poles. For example there may be a stack of between three and eight coils wound around the core in the vicinity of each pole, but at progressively greater distances.

The probe may also comprise additional sensing coils for other parameters. In an embodiment, the probe also comprises a sensing coil arranged between the poles with the longitudinal axis of the sensing coil parallel to a line joining the centers of the poles, this sensing coil being sensitive to leakage flux.

The present invention also provides a method for measuring material properties of an object of ferromagnetic material, using such an apparatus.

BRIEF DESCRIPTION OF THE DRAWINGS

Embodiments of the present invention will now be further and more particularly described, by way of example only, and with reference to the accompanying drawings, in which.

DETAILED DESCRIPTION

Probe Design

Figure 1:
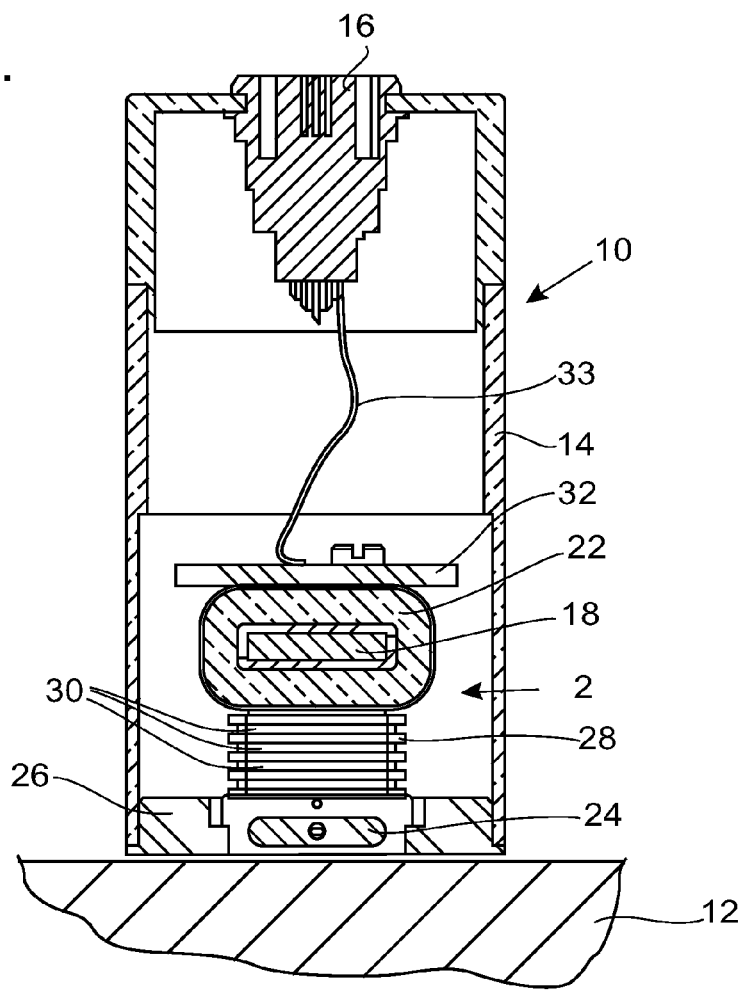
FIG. 1 shows a longitudinal sectional view of a probe for measuring stress in a material, the probe comprising an electromagnet.
Figure 2:
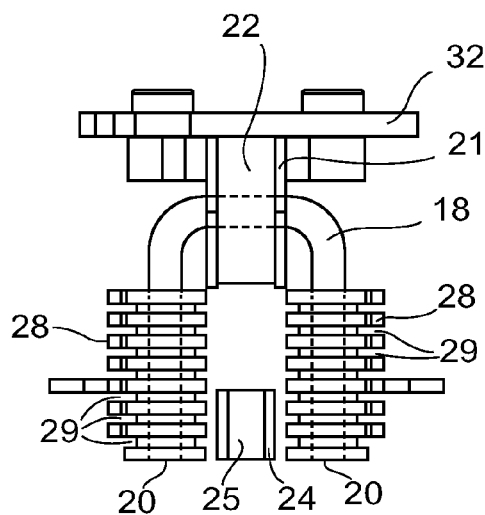
FIG. 2 shows the electromagnet of the probe of FIG. 1, viewed in the direction of arrow 2, other components not being shown.

Referring to FIG. 1, a probe 10 can be used to measure stress within a region near the surface of an object 12. The probe 10 comprises a cylindrical brass casing 14 of external diameter 40 mm and of overall height 80 mm. The upper half of the casing 14 encloses a multi-pin connector socket 16. Referring also to FIG. 2, the lower half encloses a U-core 18 of laminated high-permeability silicon/iron alloy whose pole faces 20 are separated by a gap 11 mm wide, and are each of width 3 mm, and of thickness 15 mm (out of the plane of the figure). The pole faces 20 are in the plane of the lower end of the casing 14, and are therefore exposed. Around the upper end of the U-core 18 is a former 21 on which is wound a drive coil 22 consisting of 121 turns of copper wire. This coil 22, in operation of the probe 10, is supplied with a sinusoidal drive current from an AC signal supply unit (not shown) such that the alternating magnetic field is considerably less than saturation within the adjacent region of the object 12.

Figure 3:
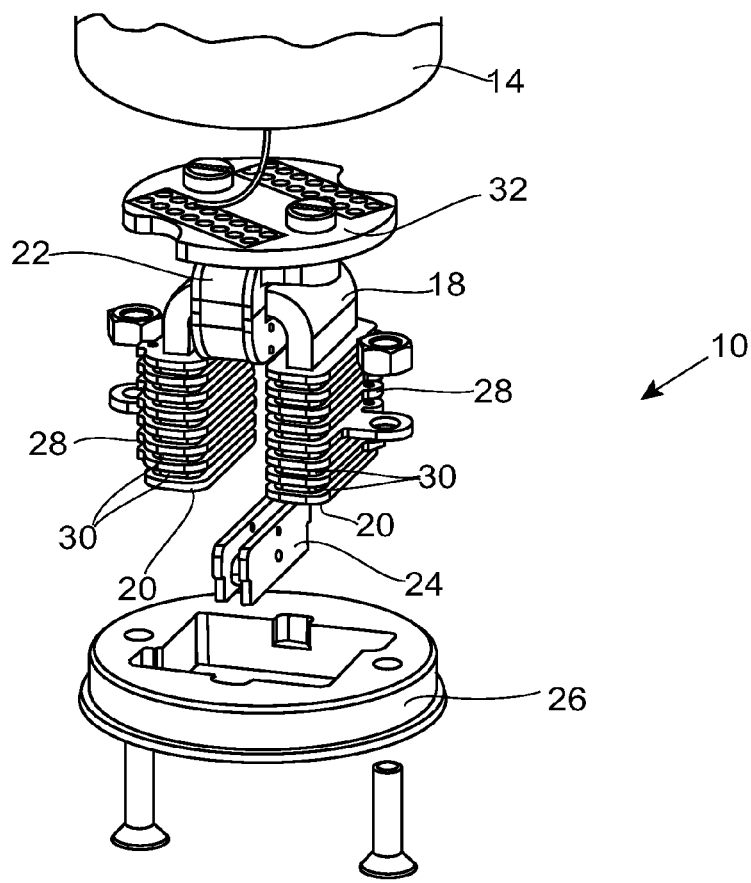
FIG. 3 shows a perspective view of the probe of FIG. 1, the housing not being shown.

Between the arms of the U-core 18 is a former 24 on which is wound a 100-turn rectangular coil 25 (see FIGS. 2 and 3), the windings lying parallel to the plane of FIG. 1 so the longitudinal axis of the coil 25 is parallel to a line between the centers of the pole faces 20. The former 24 is supported by a base plate 26 so the lower face of the coil 25 is in the plane of the pole faces 20. The coil 25 provides a signal indicative of leakage flux.

Around the portion of the U-core 18 adjacent to each pole face 20 is a multi-coil former 28 that defines seven grooves 29 spaced apart along it length. Each groove 29 locates a coil 30 (not shown in FIG. 2) consisting of forty turns of copper wire, and the coils 30 on both formers 28 are all wound in the same sense. Each coil 30 would provide signals indicative of magnetic flux through the corresponding portion of the U-core 18, which is the magnetic flux that links with the object 12, so they may be referred to as linkage flux sensor coils.

The drive coil 22, the leakage flux sensor coil 25, and each of the linkage flux sensor coils 30 are connected electrically to respective terminals of the multi-pin connector socket 16 via a terminal plate 32 mounted on top of the former 21, and wires 33 (only one is shown) from the terminal plate 32 to the multi-pin connector socket 16. Hence, in operation of the probe 10, the sinusoidal drive current can be supplied to the drive coil 22, and the resulting signals can be detected from the sensor coils 25 and 30 by an external signal processing unit (not shown).

The coils 30 are connected electrically in pairs within the probe 10, a pair being constituted by two coils 30 that are at the same distance from the pole face 20. Each coil 30 is wound in the same sense, so the ends of the wire forming the coil 30 may be identified as the start end and the finish end. The start ends of the pair of coils 30 are soldered together, while the finish ends provide the output signals for that pair of coils 30 and are therefore connected via the terminal plate 32 to respective terminals of the multi-pin connector socket 16. Thus, in this example, the multi-pin connector socket 16 provides two terminals for the drive coil 22, two terminals for the leakage flux sensor coil 25, and fourteen terminals for the seven pairs of linkage flux sensor coils 30.

It will be appreciated that the probe 10 is shown by way of example only. The dimensions of the poles 20 and their separation determines the area within the object 12 within which stress measurements are made, and the measurements are effectively averaged over that area. So in some cases, where a high spatial resolution is required, a smaller probe may be used, while in other cases where the spatial resolution is of less significance a larger probe may be used. Probes 10 of overall diameter between about 4 mm and 150 mm have been found suitable for different applications. It will also be appreciated that the skin depth depends upon the drive frequency, varying inversely with the square root of the frequency, so that the frequency at which measurements are made will determine the depth below the surface of the object 12 over which the stress is measured. For example the frequency might be selected within the range from say 5 Hz (which in mild steel would give a penetration or skin depth of about 5 mm) up to say 150 kHz (for a penetration of only about 15 microns in mild steel). Where even higher frequency measurements are required, up to 25 MHz, for example at 10 MHz, the core of the probe may be made of ferrite rather than silicon/iron alloy.

It will also be appreciated that a probe 10 might have only the drive coil 22 and the pair of coils 30 closest to the pole faces 20.

Alternative Probe Design

Figure 4:
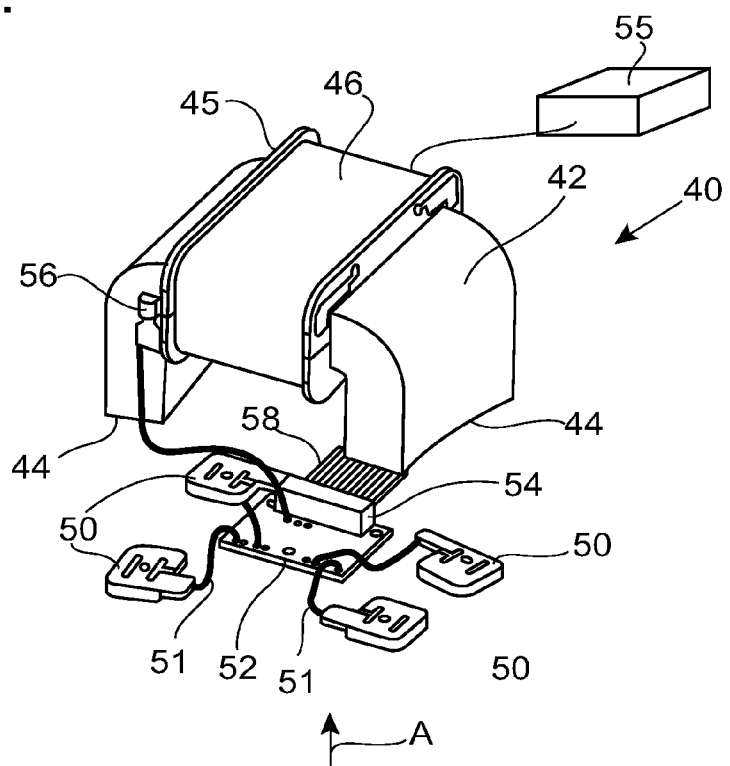
FIG. 4 shows an exploded view of an alternative probe for measuring stress in a material.

Referring now to FIG. 4 there is shown an exploded view of an alternative probe 40 for use in measuring stress in steel wires that are embedded within a nonmagnetic covering material, for example for reinforcing wires within a flexible oilfield riser. In this example each steel wire is of diameter 12 mm, and the steel wires are covered by a layer of polymer that may be 12 mm thick; more generally the steel wires may be between 4 mm and 20 mm thick, and the layer of polymer covering them may be between 4 and 20 mm thick.

The probe 40 comprises a U-core 42 of laminated high-permeability silicon/iron alloy whose pole faces 44 are separated by a gap about 60 mm wide, and are each of width 60 mm, and of thickness 18 mm. The pole faces 44 are slightly curved to conform to the outer surface of the riser. Around the upper end of the U-core 42 is a former 45 on which is wound a drive coil 46. This coil 46, in operation of the probe 10, is supplied with a sinusoidal drive current from an AC signal supply unit 55 (shown diagrammatically) such that the alternating magnetic field induced in the steel wires below the surface of the riser is considerably less than saturation.

The probe 40 also comprises four flat sensor coils 50 each wound around a square former of side 17 mm, each coil being connected by a pair of wires 51 to a printed circuit board 52 that includes a head amplifier 54. The probe 40 also includes a temperature sensor 56 that is also connected to the printed circuit board 52. A flexible multi-wire strip 58 carries output signals from the head amplifier 54 to a signal analysis unit (not shown). The sensor coils 50 are shown separated from the U-core 42, but in reality are secured to the pole faces 44 near the corners of the probe 40. They may be fixed by adhesive, or they may be secured within a frame that is fixed to the U-core 42.

Figure 5:
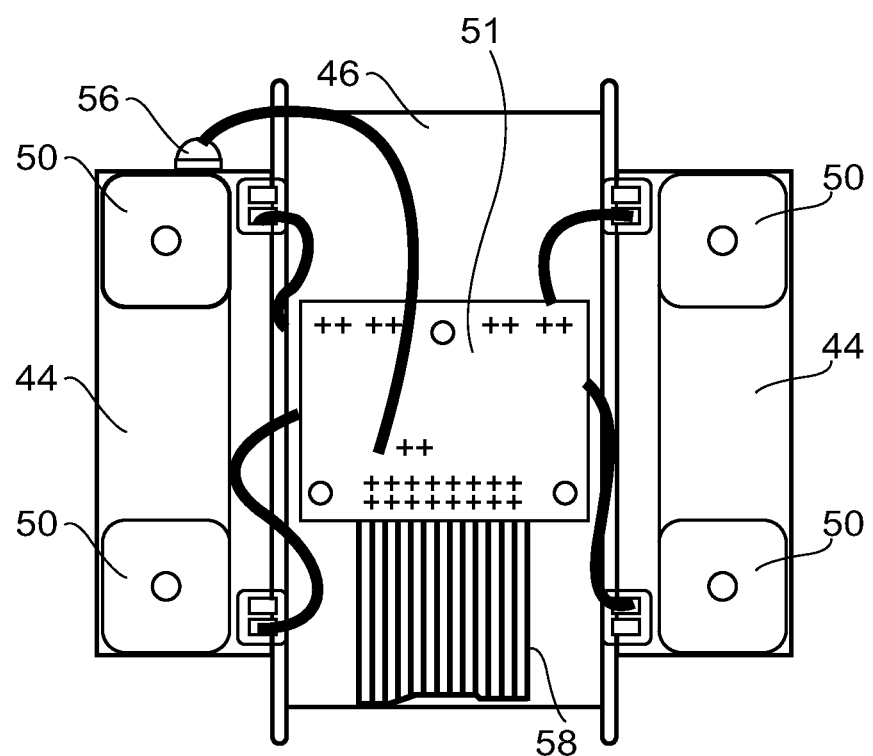
FIG. 5 shows a view in the direction of arrow A of the probe of FIG. 4 when assembled.

Referring now to FIG. 5, this shows the underside of the probe 40, with the sensor coils 50 secured to the pole faces 44. The sensor coils 50, which are approximately 17 mm square, are attached at opposite ends of the poles 44, which are 60 mm by 18 mm, and so the sensor coils 50 are at the corners of the probe 40, and on any one pole face 40 the space between one sensor coil 50 and the other is about 26 mm.

The sensor coils 50 are sufficiently small that if the probe 40 is suitably oriented each one is sensitive to a different steel wire within the riser, so that the properties of the separate steel wires can be distinguished. Hence this arrangement provides greater resolution than would be possible using a sensor coil that is overwound onto the drive coil 46.

Measurement and Analysis

A probe 10 or 40 may be used to measure stress in a ferromagnetic object by a method such as that described in EP 1 436 604. In operation the probe 10 or the probe 40 is placed adjacent to a surface of an object, and an alternating current of a desired frequency and amplitude is supplied to the drive coil 22 or 46, so the magnetic field in the object oscillates about zero with an amplitude much less than saturation. The signal components in phase and in quadrature are measured, and before the signals are processed they may be amplified and digitized.

As a preliminary setting-up step, measurements of the linkage flux signals i.e. the signals from the linking flux sensor coils 30 or 50 may first be made with the probe 10 or 40 in air; and may be made adjacent to an object of the same type of ferromagnetic material as those on which stress measurements are required, but in which the stresses are negligible. The in-phase and quadrature components of the flux linkage signal (i.e. the component in phase with the drive current, and the component differing in phase by) 90° may each be backed off to zero, and the backing off values would then be fixed. During all subsequent measurements the flux linkage components would be backed off by these same amounts (i.e. subtracting a signal equal to the component observed at a stress-free location). This backing off step is not required if the signals are digitized before resolving the in-phase and quadrature components.

The values of the stresses in the directions of the principal stress axes can be determined from experimental measurements of the in-phase and quadrature components of the flux linkage signals with the probe 10 or 40 oriented in those directions. This requires calibration of the probe 10 or 40, taking measurements on a sample of material of the same type as the object, while subjecting it to a variety of different stresses. This may be done with a rectangular strip sample in a test rig, flux linkage measurements being made at the center of the sample where the principal stress direction is aligned with the axis of the test rig. One set of measurements would be made at progressively larger values of lift-off, L, but with no stress, S. This gives a fixed-stress contour in the impedance plane (i.e. in a graph of the quadrature component against the in-phase component). Similar fixed-stress contours may be obtained for other values of stress, more particularly both for tension and compression. Measurements would then be made at a range of different fixed values of lift-off, L, with varying stresses, S (both compression and tension), providing one or more sets of fixed-lift-off contours. It is found that all the contours are curved, and that the two sets of contours intersect each other.

After calibrating the probe 12 in this manner, stress measurements can then be taken by placing the probe 10 or 40 adjacent to the object in which stress is to be measured. The calibration contours enable the changes due to lift-off to be readily distinguished from changes due to stress. Any particular position in the impedance plane (i.e. in the graph of quadrature against in-phase components) corresponds to a particular value of stress and a particular value of lift-off. The mapping between (in-phase, quadrature) coordinates and (stress, lift-off) coordinates may be carried out graphically, referring to such contours, or by calculation.

In some situations the orientation of the principal stress axes is known, for example in the steel reinforcing wires within a flexible riser the principal stress axis is along the length of the wire. If the principal stress axes are not known, they may be determined by gradually rotating the probe 10 through a complete turn, taking measurements at several different orientations of the probe. The orientation of the line joining the centers of the pole faces 20 or 44 is referred to as the orientation of the probe 10 or 40. The linkage flux signals vary sinusoidally with probe orientation, and the orientations at which they have peak values correspond to the orientations of the principal stress axes.

The value of stress found in this way is, it will be appreciated, the uniaxial stress that would provide that value of the linkage flux signal. If the stresses are actually biaxial, then a further calibration must be carried out with a cross-shaped sample in a test rig, linkage flux measurements being made at the center of the sample where the principal stress directions are aligned with the axes of the test rig. Hence a graph or map may be obtained for a range of values of stress on one axis (say the x-axis) and for a range of values of stress in the other axis (say the y-axis), with contours each of which shows the values of biaxial stress that give a particular value of apparent uniaxial stress along the x-axis; and a similar graph may be obtained with contours showing values of biaxial stress that give a particular value of apparent uniaxial stress along the y-axis. Hence from measurements of apparent uniaxial stress along the two principal stress axes obtained as described earlier, the biaxial stress can be determined.

It will again be appreciated that the biaxial stress may be determined either graphically or by calculation in this way. Apparent values of uniaxial stress (in MPa) may be used for this purpose, or alternatively the numerical value of the linkage flux signal (in mV), either the in-phase or quadrature value, obtained by eliminating the effect of lift-off as described above, may be used.

Experimental Results 1

The probe according to an embodiment of the present invention has been found to be considerably more sensitive to material properties (such as stress) than a probe in which the sensor for linkage flux is a coil overwound on the drive coil. For example a comparison has been made between measurements made using the probe 40 and a probe with an identical U-core 42 and drive coil 46, but using an overwound coil (i.e. a coil wound onto the drive coil 46) as the linkage flux sensor. Measurements were made of the stress in a number of steel wires embedded in a flexible riser, and two positions were located at which the stresses were respectively high and low. The measured values of stress at those positions, S1 and S2, were compared to the average stress along the observed length of riser, S. The fractional change of signal (S1-S2)/S is a measure of the sensitivity to changes in stress; in Table 1 the values obtained with the probe 40 are referred to as A, while those obtained with the overwound coil are referred to as B. All these measurements were made at 960 Hz; the results at frequencies down to 35 Hz were similar, increasing by no more than 20% over that frequency range.

TABLE 1

| Lift-off/mm | fractional change A | fractional change B |
|---|---|---|
| 14 | 0.060 | 0.0045 |
| 25 | 0.036 | 0.0022 |
| 35 | 0.020 | 0.0014 |
| 45 | 0.009 | 0.0009 |

It will be appreciated that in each case the sensitivity to stress decreases as the liftoff increases. Surprisingly, the sensitivity to stress obtained using the probe 40 with the sensor coils 50 is at least ten times greater than that using the over-wound sensor coil.

Experimental Results 2

Measurements have been made using the probe 10 observing stress in a specimen of steel rail that could be subjected to known stresses, both in compression and in tension. Before making any measurements on the specimen, measurements were made in air at a range of different frequencies (from 70 Hz up to 2950 Hz). The probe 10 was orientated along the principal stress axis of the specimen, so that no rotation of the probe was required; and the probe 10 was clamped firmly onto the specimen, to ensure there was no lift-off. The in-phase signal components and the quadrature signal components (without backing-off) were both normalized by dividing by the quadrature signal component with the probe in air.

The signals were taken from the pair of coils 30 nearest to the pole faces 20 (reference P); and also from the next-but-one pair of coils 30 (reference Q), which is the third pair of coils 30; and from the fifth pair of coils 30 (reference R); and from the seventh pair of coils 30 (reference S). Under all circumstances, the closer the coils 30 are to the pole faces 20 the less are the signals before normalization, so the signals under reference P are less than those under reference S. This may be because some of the flux generated by the driver coil 22 passes directly between the two arms of the U-core 18, acting as leakage flux, rather than passing through the U-core 18 and through the object 12.

The results of these measurements are summarized in Table 2, showing the sensitivity to changes in stress for these sensor coils. The sensitivity value is proportional to the change of position in the normalized impedance plane due to a given change of stress.

TABLE 2

| Coil Pair | Frequency/Hz | Stress sensitivity |
|---|---|---|
| P | 70 | 13 |
| Q | 70 | 8 |
| R | 70 | 5.5 |
| S | 70 | 4.5 |
| P | 2950 | 12 |
| Q | 2950 | 7 |
| R | 2950 | 5 |
| S | 2950 | 4.5 |

For any one pair of coils 30 (P, Q, R or S), the sensitivity to stress decreases only slightly as the frequency increases. But at a fixed frequency it is clear that the coil pairs P are considerably more sensitive to stress than the coil pairs S, that is to say the sensitivity decreases as the distance of the coil pair from the pole faces increases. So although the signals from the coil pairs P are less than those from the other coil pairs, the sensitivity of those signals to changes in stress in the material is significantly greater.

Alternative Probe Design

Figure 6:
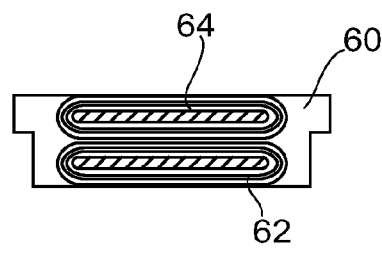
FIG. 6 shows a sectional view of an alternative sensor for use in the probe of FIG. 1.

The probe 10 is described above as incorporating a single leakage flux sensing coil 25 on a former 24. Referring now to FIG. 6, a probe may instead incorporate a former 60 carrying a pair of leakage flux sensing coils 62 and 64. The former 60 would be mounted between the arms of a U-core of magnetic material, around which is wound a drive coil. The drive coil, as described above, in operation of the probe would be supplied with a sinusoidal drive current from an AC signal supply unit (not shown) such that the alternating magnetic field is considerably less than saturation within the adjacent region of the object 12.

The windings of the leakage flux sensing coils 62 and 64 are such that the longitudinal axis of each coil 62 and 64 is parallel to a line between the centers of the pole faces of the U-core. The former 60 would be supported such that the lower surface of the lower coil 62 is in the plane of the pole faces. Each coil 62 and 64 would consequently provide a signal indicative of leakage flux.

It has been found that the lower coil 62, that is to say the leakage flux sensing coil 62 that is closest to the surface of the object 12, provides a signal that is sensitive to both lift-off and also to material properties within the object 12. The upper coil 64 is also sensitive to lift-off, but is much less sensitive to material properties within the object 12. Hence by connecting the sensing coils 62 and 64 in opposition, or by subtracting the signal from the upper coil 64 from the signal from the lower coil 62, an output signal may be obtained that is primarily sensitive to material properties (such as stress). This arrangement also suppresses other common mode sources of error, for example due to external magnetic fields.

It should be appreciated that a probe may incorporate such sensing coils 62 and 64 as its only sensing coils. Alternatively a probe may include both leakage flux sensing coils 62 and 64, and also linkage flux sensor coils, such as the coils 30 of the probe 10 of FIG. 1. Indeed the sensing coils 62 and 64 might be used in the probe 10, by replacing the former 24 and the coil 25 with the former 60 and coils 62 and 64.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An apparatus for measuring material properties of an object of ferromagnetic material, the apparatus comprising:
    a probe comprising:
        an electromagnet core defining two spaced-apart poles for inducing a magnetic field in the object, so faces of the two spaced-apart poles define four corners of the probe;
        a drive coil wound around the electromagnet core; and
        at least four sensing coils configured to sense the magnetic flux density that links the electromagnet core and the object, wherein at least two of the at least four sensing coils are arranged in the vicinity of each of the two spaced-apart poles; and
    an alternating current supply configured to supply an alternating electric current to the drive coil to generate an alternating magnetic field in the electromagnet core and consequently in the object,
    wherein two of the at least four sensing coils are arranged on the face of each pole, each of the two sensing coils is between the face of the respective pole and a surface of the object, and each of the two sensing coils are attached at opposite ends of the face of the respective pole so that one sensing coil is near each of the four corners of the probe, and
    wherein the object is a steel wire embedded within a non-magnetic covering material, in a flexible oilfield riser, and the two sensing coils arranged on the face of each pole are sufficiently small that, if the probe is suitably oriented, each of the two sensing coils is sensitive to a different steel wire within the flexible oilfield riser.

2. The apparatus as claimed in claim 1, further comprising sensing coils wound around the electromagnet core adjacent to the two spaced-apart poles.

3. The apparatus as claimed in claim 2, wherein at any one of the two spaced-apart poles there are a plurality of sensing coils at different distances from the respective pole.

4. The apparatus as claimed in claim 2, further comprising at least one matched pair comprising a sensing coil in the vicinity of one pole of the two spaced-apart poles connected in series with a sensing coil in the vicinity of the other pole of the two spaced-apart poles to provide an output.

5. The apparatus as claimed in claim 4, wherein the sensing coils of the at least one matched pair are wound or connected such that equal magnetic field changes directed towards the two spaced-apart poles would produce no net output.

6. The apparatus as claimed in claim 1, wherein the probe further comprises additional sensing coils for other parameters.

7. The apparatus as claimed in claim 6, wherein the probe further comprises a leakage flux sensing coil arranged between the two spaced-apart poles with the longitudinal axis of the leakage flux sensing coil parallel to a line between the centers of the two spaced apart poles, the leakage flux sensing coil being sensitive to leakage flux.

8. The apparatus as claimed in claim 7, wherein the probe further comprises two leakage flux sensing coils sensitive to leakage flux, one of these two leakage flux sensing coils being closer to a plane of the two space-apart poles than the other of these two leakage flux sensing coils.

9. The apparatus as claimed in claim 1, further comprising at least one matched pair comprising a sensing coil in the vicinity of one pole of the two spaced-apart poles connected in series with a sensing coil in the vicinity of the other pole of the two spaced-apart poles to provide an output.

10. The apparatus as claimed in claim 9, wherein the sensing coils of the at least one matched pair are wound or connected such that equal magnetic field changes directed towards the two spaced-apart poles would produce no net output.

11. A method for measuring stress in an object of ferromagnetic material, using an apparatus including a probe including an electromagnet core defining two spaced-apart poles for inducing a magnetic field in the object, so faces of the two spaced-apart poles define four corners of the probe, a drive coil wound around the electromagnet core, and at least four sensing coils configured to sense the magnetic flux density that links the electromagnet core and the object, wherein at least two of the at least four sensing coils are arranged in the vicinity of each of the two spaced-apart poles, and an alternating current supply configured to supply an alternating electric current to the drive coil to generate an alternating magnetic field in the electromagnet core and consequently in the object, wherein two of the at least four sensing coils are arranged on the face of each pole, each of the two sensing coils is between the face of the respective pole and a surface of the object, and each of the two sensing coils are attached at opposite ends of the face of the respective pole so that one sensing coil is near each of the four corners of the probe, the method comprising:
  placing the probe adjacent to the surface of the object;
  applying the alternating electric current to the drive coil so the magnetic field in the object oscillates about zero with an amplitude much less than saturation;
  detecting signals from the sensor coils;
  measuring signal components of the signals in phase and quadrature relative to the alternating electric current; and
  distinguishing changes in the signal components due to lift-off from changes due to stress, and hence deducing the stress in the object.

12. The method as claimed in claim 11, wherein the object is a steel wire embedded within a non-magnetic covering material, in a flexible oilfield riser.

13. The method as claimed in claim 12, wherein the two sensing coils arranged on the face of each pole are sufficiently small that, if the probe is suitably oriented, each of the two sensing coils is sensitive to a different steel wire within the flexible oilfield riser.

14. An apparatus for measuring material properties of an object of ferromagnetic material, the apparatus comprising:
  a probe comprising:
    an electromagnet core defining two spaced-apart poles for inducing a magnetic field in the object;
    a drive coil wound around the electromagnet core; and
    at least two sensing coils configured to sense the magnetic flux density that links the electromagnet core and the object, wherein at least one of the at least two sensing coils is arranged in the vicinity of each of the two spaced-apart poles; and
  an alternating current supply configured to supply an alternating electric current to the drive coil to generate an alternating magnetic field in the electromagnet core and consequently in the object,
  wherein the at least two sensing coils are wound around the electromagnet core adjacent to the two spaced-apart poles to form at least one matched pair, the at least one matched pair comprising a sensing coil in the vicinity of one pole of the two spaced-apart poles connected in series with a sensing coil in the vicinity of the other pole of the two spaced-apart poles to provide an output, the sensing coils of each of the at least one matched pair being wound or connected such that equal magnetic field changes directed towards the two spaced-apart poles would produce no net output.

15. The apparatus as claimed in claim 14, wherein at any one of the two spaced-apart poles there are a plurality of sensing coils wound around the electromagnet core at different distances from the respective pole.

16. A method for measuring stress in an object of ferromagnetic material using an apparatus according to claim 14, the method comprising:
  placing the probe adjacent to the surface of the object;
  applying the alternating electric current to the drive coil so the magnetic field in the object oscillates about zero with an amplitude much less than saturation;
  detecting signals from the sensor coils;
  measuring signal components of the signals in phase and quadrature relative to the alternating electric current; and
  distinguishing changes in the signal components due to lift-off from changes due to stress, and hence deducing the stress in the object.

17. The apparatus as claimed in claim 14, wherein the probe further comprises additional sensing coils for other parameters.

18. The apparatus as claimed in claim 17, wherein the probe further comprises a sensing coil arranged between the two spaced-apart poles with the longitudinal axis of the sensing coil parallel to a line between the centers of the two spaced-apart poles, this sensing coil being sensitive to leakage flux.

19. The apparatus as claimed in claim 18, wherein the probe further comprises two sensing coils sensitive to leakage flux, one of these two sensing coils being closer to a plane of the two spaced-apart poles than the other of these two sensing coils.

20. The apparatus as claimed in claim 14, wherein the probe further comprises at least four flat sensing coils configured to sense the magnetic flux density that links the electromagnet core and the object, wherein at least two of the at least four flat sensing coils are arranged in the vicinity of each of the two spaced-apart poles.

21. The apparatus as claimed in claim 20, wherein two of the at least four flat sensing coils are arranged on the face of each pole, each of the two flat sensing coils is between the face of the respective pole and a surface of the object, and each of the two flat sensing coils are attached at opposite ends of the face of the respective pole so that one flat sensing coil is near each of the four corners of the probe.

22. The apparatus as claimed in claim 21, wherein the object is a steel wire embedded within a non-magnetic covering material, in a flexible oilfield riser, and the two flat sensing coils arranged on the face of each pole are sufficiently small that, if the probe is suitably oriented, each of the two flat sensing coils is sensitive to a different steel wire within the flexible oilfield riser.

* * * * *